United States Patent
Plöckl

(10) Patent No.: US 10,578,537 B2
(45) Date of Patent: Mar. 3, 2020

(54) METHOD FOR MEASURING THE PROPERTIES OF PARTICLES IN A MEDIUM AND A DEVICE FOR MEASURING THE PROPERTIES OF PARTICLES IN A FLUE GAS

(71) Applicant: SINTROL OY, Helsinki (FI)

(72) Inventor: Manfred Plöckl, Holzkirchen (DE)

(73) Assignee: Sintrol Oy, Helsinki (FI)

( * ) Notice: Subject to any disclaimer, the term of this patent is extended or adjusted under 35 U.S.C. 154(b) by 0 days.

(21) Appl. No.: 16/090,224

(22) PCT Filed: Mar. 30, 2017

(86) PCT No.: PCT/FI2017/050224
§ 371 (c)(1),
(2) Date: Sep. 29, 2018

(87) PCT Pub. No.: WO2017/168052
PCT Pub. Date: Oct. 5, 2017

(65) Prior Publication Data
US 2019/0086315 A1 Mar. 21, 2019

(30) Foreign Application Priority Data
Mar. 30, 2016 (FI) ..................... 20160074

(51) Int. Cl.
*G01N 15/02* (2006.01)
*G01N 15/00* (2006.01)

(52) U.S. Cl.
CPC . *G01N 15/0211* (2013.01); *G01N 2015/0046* (2013.01)

(58) Field of Classification Search
CPC ............... G01N 15/0211; G01N 2015/0046
USPC ............................................ 356/336
See application file for complete search history.

(56) References Cited

U.S. PATENT DOCUMENTS

| 3,553,462 A | * | 1/1971 | Johnson | G01N 21/532 250/565 |
| 4,676,641 A |   | 6/1987 | Bott | |
| 5,009,493 A | * | 4/1991 | Koch | G01N 21/031 356/246 |
| 5,065,025 A | * | 11/1991 | Doyle | G01N 21/05 250/343 |
| 5,286,452 A | * | 2/1994 | Hansen | G01N 33/4905 422/73 |
| 5,360,980 A |   | 11/1994 | Borden et al. | |
| 5,854,685 A | * | 12/1998 | Levine | G01J 3/1838 356/440 |
| 6,563,583 B2 | * | 5/2003 | Ortyn | C07K 1/047 356/399 |

(Continued)

FOREIGN PATENT DOCUMENTS

EP 0768521 A1 4/1997

*Primary Examiner* — Roy M Punnoose
(74) *Attorney, Agent, or Firm* — Seppo Laine Oy

(57) ABSTRACT

The invention relates to a method for determining properties of particles in a medium by measuring scattering of a light ray guided through the medium. The light ray (2) can be led through a scattering zone (4) more than once. Both the scattered (5) and unscattered light are measured using the same sensor (6). The invention also relates to a measuring device for measuring the properties of particles in a medium, such as flue gas.

15 Claims, 3 Drawing Sheets

(56) References Cited

U.S. PATENT DOCUMENTS

| | | | |
|---|---|---|---|
| 6,580,504 B1* | 6/2003 | Ortyn | G01J 3/2803 |
| | | | 356/246 |
| 6,947,136 B2* | 9/2005 | Ortyn | G01J 3/2803 |
| | | | 356/246 |
| 7,087,885 B1 | 8/2006 | Yamaguchi | |
| 7,449,694 B2* | 11/2008 | Yi | G01N 21/031 |
| | | | 250/339.13 |
| 7,502,110 B2* | 3/2009 | Saunders | G01N 15/1459 |
| | | | 356/336 |
| 8,345,254 B2* | 1/2013 | Prystupa | G01N 21/86 |
| | | | 356/432 |
| 8,479,559 B2* | 7/2013 | Miklos | G01N 21/031 |
| | | | 250/339.07 |
| 10,241,043 B2* | 3/2019 | Nakai | G01N 15/06 |
| 2002/0057432 A1* | 5/2002 | Ortyn | C07K 1/047 |
| | | | 356/338 |
| 2003/0137661 A1* | 7/2003 | Ortyn | G01J 3/2803 |
| | | | 356/338 |
| 2006/0017926 A1* | 1/2006 | Pochy | G01N 15/0205 |
| | | | 356/338 |

* cited by examiner

METHOD FOR MEASURING THE PROPERTIES OF PARTICLES IN A MEDIUM AND A DEVICE FOR MEASURING THE PROPERTIES OF PARTICLES IN A FLUE GAS

FIELD

The present invention relates to a method for measuring properties of particles contained in a medium on the basis of scattering of a light ray travelling through the medium in a scattering zone, a measuring device for measuring properties of particles in a medium, such as particles in a flue gas and a measuring duct arranged in parallel with an actual flue, the measuring duct having a measuring device as mentioned.

BACKGROUND

The field of the method according to the invention is the study of the properties of the particles in a medium, such as a gas or a liquid. The field of the device according to the invention is the study of the properties of the particles contained as particles of solids in gases, such as flue gases. The device according to the invention is also suitable for studying the properties of particles of relatively clean gases, such as clean room and occupational air.

The properties of particles in gases and liquids are generally measured by observing the scattering of a ray of light as it travels through a medium. When studying flue gases, the measuring device is generally located in a flue, so the particles are passing the measurement area which is prone to misalignment and thus may lead to inaccurate measurements. A laser is generally used as the source of light when forming the ray of light.

Problems are caused by the contamination of the measuring device by impurities and moisture in the flue gas. Contamination of the optical elements causes variations in the intensity of light. Due to contamination, compensation is required to achieve the correct measurement results. Attempts have been made to prevent contamination of the optical elements by guiding the ray of light to the flue gas and away from it through an opening, from which a clean gas, such as air, is blown to flow away from the optical elements and thus prevent the flue gas from meeting the element. This arrangement endangers the accuracy of the measurement, because the blown clean gas dilutes the flue gas and causes unintended refractions caused by purge air, flue gas layers and temperature gradients.

A laser produces monochromatic light, the scattering angle of which depends on the wavelength of the light. The wavelength of the light produced by a laser depends on the temperature. In addition, the intensity of the light produced by a laser depends on the light source and electronics temperature. Temperature compensation is therefore needed. The scattering angle and intensity of the monochromatic light produced by a laser changes as the size of the particles changes. Both the wavelength of the scattered light and the intensity of the light depend on the size and colour, and therefore the reflectivity of the particles.

It is known to study the particles contained in a medium by using as a light source a light source emitting several wavelengths, for example a LED (Light Emitting Diode) light source emitting white light. As the light emitted by the light source contains several wavelengths, the wavelength of the light scattered by the particles will not significantly depend on the size of the particles.

From the aforementioned physical phenomena it follows that various data can be measured, decided on, and calculated based on the intensity, scattering angle, and wavelength of the light scattered from the particles in a medium. For example, it is possible to determine the concentration of the particles, the particles' size, and the number of particles.

A conventional particle-measuring device, which is located in a flue, and uses a laser as a light source, is large and heavy. It requires access for maintenance and cleaning. The art is represented by patent publication U.S. Pat. No. 4,024,407.

EP 1969997 and EP 0768521 disclose light absorption-based measurement methods and devices for the measurement of gases. The documents also disclose ways to extend the path of light to enhance absorption and preventing scattered light from entering the absorption sensor.

It is known to place the measuring device in a small-dimension flue, a measuring duct, parallel to the actual flue. A conventional measuring device located in a measuring duct requires a measuring chamber around it that is significantly wider than the typical pipe size of a measuring duct. A flue-gas flow, corresponding to that in the actual flue, is attempted to be arranged in the measuring chamber.

Accurate and reliable measurement requires not only the measurement of scattered light but also the measurement of unscattered light. The measurement of unscattered light is required, for example, for calibrating the measuring device and monitoring the contamination of the measuring device's optics.

SUMMARY OF INVENTION

It is an aim of the invention to remove at least a part of the problems relating to the art and to provide a method, by means of which the properties of the particles contained in a medium can be studied.

It is another aim of the invention to create a small-sized measuring device suitable for studying the particles in a wide range of concentrations, from flue gases to clean rooms.

The above aims can be achieved by arranging the light ray used for measuring to travel along a route deviating from a straight line, in such a way that the light ray is guided perpendicular through the medium being studied in the scattering zone. If there are particles in the medium, part of the light will scatter. The intensity of the light scattered at a chosen angle is measured using a sensor.

More particularly, in one aspect, there is provided a method for measuring properties of particles contained in a medium on the basis of scattering of a light ray travelling through the medium in a scattering zone. The method comprises guiding the light ray through the scattering zone more than once, whereby a portion of light is scattered, and measuring both the scattered light and the unscattered light using the same sensor.

The light ray that has penetrated the medium in a straight line is guided to travel again through the scattering zone in such a direction that the light ray that has again penetrated the scattering zone along a straight line ends up being measured by the same sensor that measures scattered light. Entry to the sensor by the light ray that has penetrated the scattering zone along a straight line can also be prevented when doing zero and comparison checks.

Depending on whether information is desired on the concentration of the particles, the size of the particles, or the number of the particles, it is possible to select parameters, such as the modulation, wavelength of the light source, the mono- or polychromaticity of the light source, the scattering angle being studied, and the wavelengths being studied of the scattered light. The wavelength of the light source is typically in the range of visible light. However, the wavelength of the ray can, within the scope of the invention, be any electromagnetic radiation whatever that has the desired scattering property. Correspondingly, the radiation source can be any that is suitable for the purpose.

The present measuring duct comprises a measuring device as herein described and continues through the measuring device with essentially the same dimensions as it comes to the measuring device from the actual flue.

In one aspect of the invention, which can be implemented as such or, in particular, combined with the present same-sensor measurement principle, there is provided method for measuring concentration characteristics of particles in relation to particle size contained in a medium on the basis of scattering of a light ray travelling through the medium in a scattering zone. The method comprises modulating in sequence multiple light sources with different wave lengths, whereby different particle sizes in the medium scatter differently the different wave lengths, detecting the scattered light with multiple sensors to provide multiple sensor signals, and determining using the sensor signals concentration characteristics of at least two different particle size fractions of the medium.

Considerable advantages are obtained with the invention compared to conventional methods.

A small-sized measuring device can be made to operate using a light source with a lower power than that of a laser. Using a light source producing a white light, for example, a white LED (Light Emitting Diode), achieves the advantage that the variation of the wavelength of the light according to temperature need not be taken into account.

Temperature compensation is easier with a polychromatic light source compared with using a laser because detecting several wavelengths is naturally not affected by wavelength- and temperature drift.

The measuring device can be used in connection with a measuring duct parallel to the actual flue but it does not require an extensive measuring chamber. The measuring device can be constructed around the measuring duct. The measuring duct continues with essentially the same dimensions through the measuring device. It is advantageous, if the measuring duct's flow is made to correspond to that in the actual flue. Part of the measuring duct inside the measuring device can also be referred to as a scattering zone. The measuring device can be installed between the normal pipe flanges of the pipes forming the measuring duct. Such a measuring device can be easily accessed from all directions. The measuring device can therefore be serviced, for example, cleaning and calibrated, without detaching it from the measuring duct.

The contamination of the optical elements of the measuring device can be prevented, without endangering measurement accuracy, in the following manner: from the opening, from which the light ray used for measurement reaches the flue gas or comes from it, a flow of clean gas is not blown out, or only a weak flow is blown. Instead, a laminar, or nearly laminar flow of clean gas, such as air, is blown past the opening. The flow of clean gas isolates the light opening from the hot and dirty flue gas. The flow of clean gas prevents dirt from reaching the optical elements of the measuring device. It also cools the measuring device and, by isolating, prevents the flue gas from heating the measuring device. Because of this, the flue gas travelling in the measurement duct can be overheated before the measuring device to such a high temperature that the water contained in the flue gas evaporates and stays over dew point at the measuring point.

Water drops in the flue gas interfere with the measurement of the number of particles, but water vapour does not interfere. If the flow of clean gas is allowed to mix with the flue gas, it mixes only after the measurement point, when the clean gas no longer affects the measurement result.

In the following, the invention is described in greater detail with reference to the accompanying drawings.

EMBODIMENTS

Figure 1:
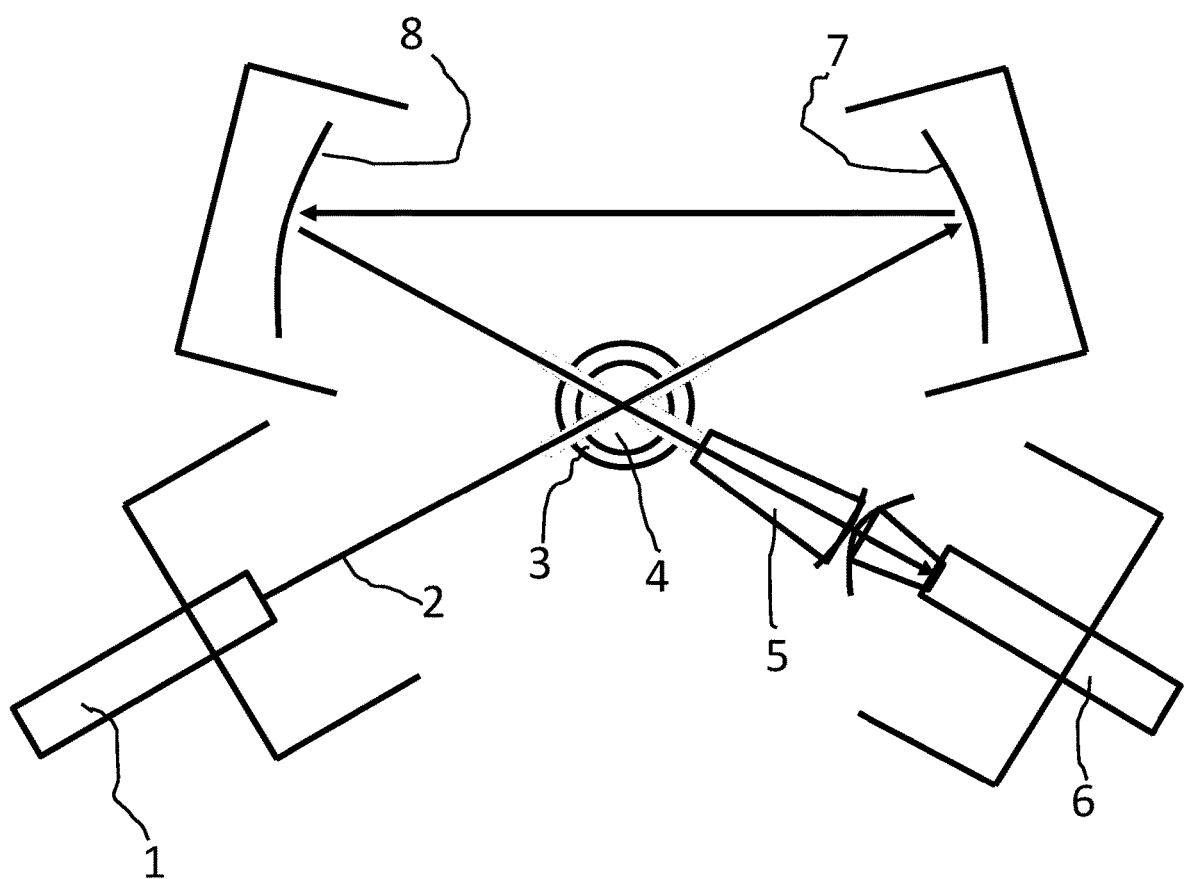
FIG. 1 shows a simplified diagram of one preferred embodiment of the invention.

The measuring device of FIG. 1 is in particular intended for studying the mass flow of particles in a flue gas.

Component 1 is a light source, from which a light ray 2 leaves. A clean-gas duct 3 surrounds a measuring duct 4, in which flue gas flows. At the location of the light rays there are openings in the walls of both ducts. The light 5 scattered from the particles in the flue gas is detected by a light sensor 6. The light ray that has penetrated the measuring duct (scattering zone) is reflected through the mirrors 7 and 8 again through the measuring duct and ends up at the light sensor 6.

A light ray 2 is made, with the aid of mirrors 7 and 8, to travel in a route deviating from a straight line. The same sensor 6 is used to measure both the forwards scattered light 5 and the unscattered light.

The light ray 2 is led at a high intensity through the measuring duct 4. When the light strikes particles in the flue gas, part of the light scatters. Some of the forwards scattering light ends up on the route 5 and is measured by the sensor 6. The unscattered part of the light ray 2 proceeds in a straight line and travels through the mirrors 7 and 8 again through the measuring duct 4, and is detected by the sensor 6. The intensity of the light ray must be reduced so that it can be measured using the same sensor as the scattered light. The reduction can be in connection with the mirrors 7 and 8, or using filters or dimmers.

There is space on the route of the light ray, when it has penetrated the measuring duct for the first time, for various optical devices, known per se, as required. They can be required, for example, for the calibration of the measuring device, for monitoring contamination, for adapting the intensity of the light ray to the sensor, or for preventing the progress of the light beam. When the light ray travels again through the measuring duct 4, its scattering is no longer of importance. Because the intensity of the ray is small, the intensity of the scattering is infinitesimally small, and only a small part of that can end up at the light sensor 6.

In a measuring device built for real use, the light ray shown in the figures can be a beam of rays of a varying diameter, which is guided with the aid of various optical elements, such as, for example, lenses, filters, shutters, dimmers, partly or fully reflecting mirrors, and optical fibres.

According to one embodiment, the light ray 2 is guided from the light source 1 through the scattering one of the measurement duct 4, for the first time, whereby a portion of light is scattered from particles contained in the medium, and guiding part of the scattered light 5, i.e. light scattered to a chosen angle to the sensor 6. The angle can be e.g. 10-80 degrees, in particular 20-70 degrees with respect to the direction of the original light ray 2. Unscattered light continues to a first mirror 7, from which it is guided past the scattering zone 4 to a second mirror 8. From the second mirror 8, the light is guided again along a straight line for the second time perpendicular through the scattering zone 4 towards the sensor 6. Thus, the unscattered light travels an X-shaped path light within the scattering zone 4 essentially transverse to the direction of gas flow. The light openings, and optionally clean gas flows, have been arranged to the measurement duct in locations corresponding to the locations of the light source 1, the mirrors 7, 8 and the sensor 6 to allow the described light propagation and measurement of unscattered and scattered light simultaneously.

Figure 2:
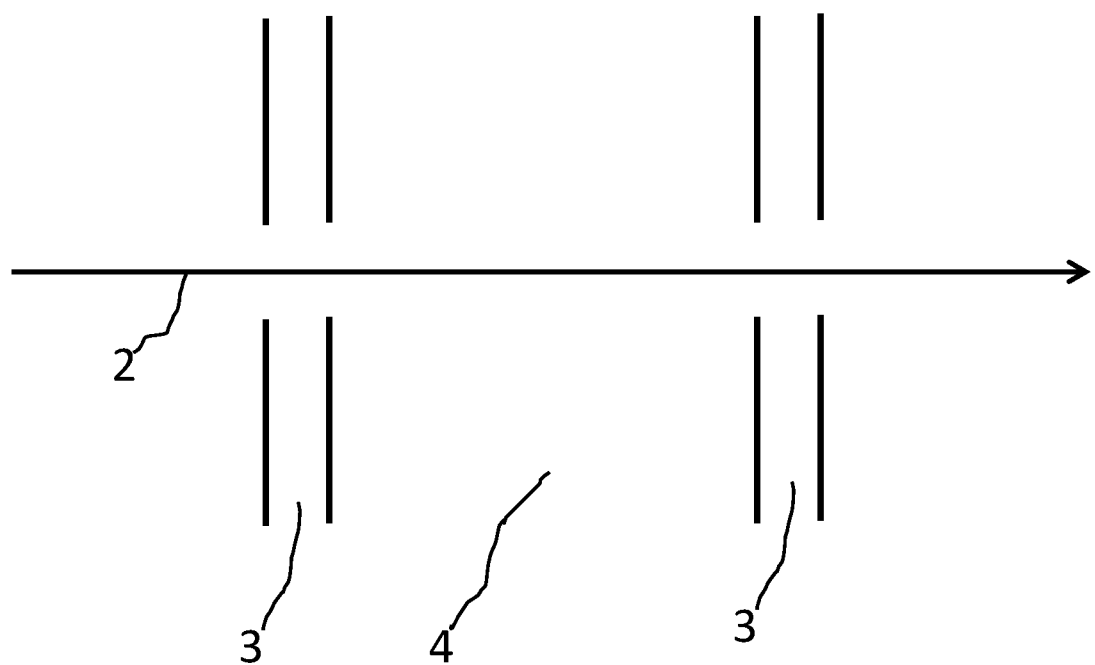
FIGS. 2 and 3 illustrate embodiments for conducting of clean gas past light openings to prevent contamination of optical elements.

FIG. 2 shows, from another direction, how the light ray 2 travels from the openings in the wall through the clean-gas duct 3 and the measuring duct 4.

Figure 3:
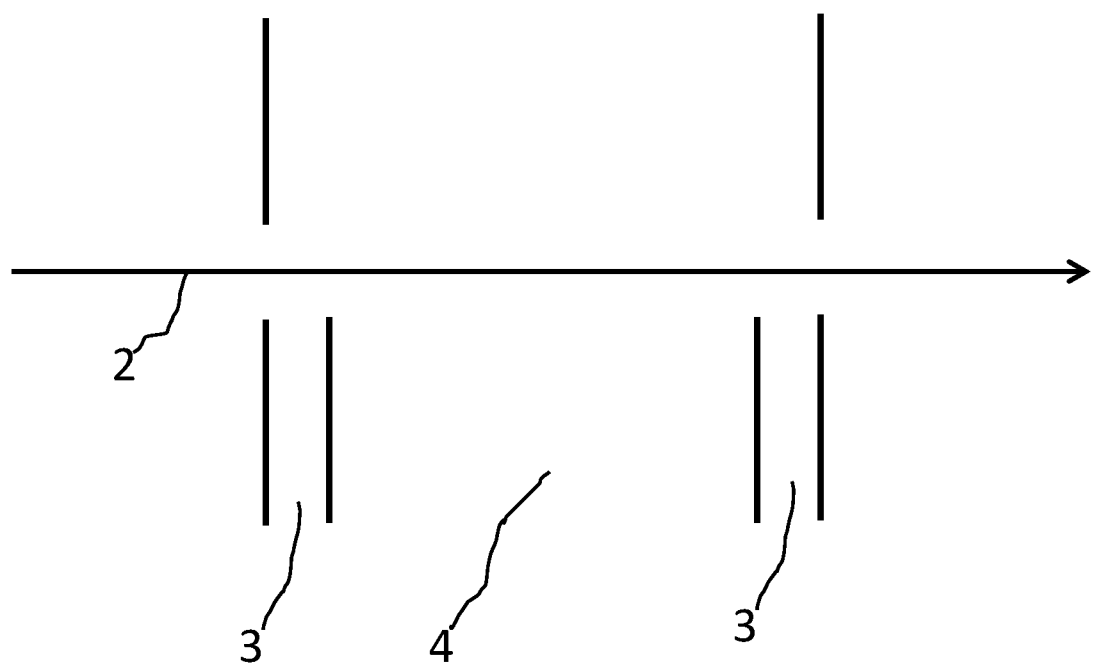

FIG. 3 shows an alternative construction, in which the clean-gas duct 3 joins the test duct 4 immediately before the light ray.

It is important in the solutions shown in FIGS. 2 and 3 that the clean gas is blown past each light opening in the measuring duct 4. The flow of clean gas prevents dirt from travelling from the light opening to the measuring device and reduces the heating effect of the flue gases on the measuring device. If the clean gas is allowed to mix with the flue gas, mixing takes place only after the measuring point and does not interfere with measurement.

As referred to above, in one aspect of the invention, there is provided a method for measuring concentration characteristics of particles in relation to particle size contained in a medium on the basis of scattering of a light ray 2 travelling through the medium in a scattering zone 4 using multiple light sources and multiple sensors. The multiple light sources are modulated so that they produce a sequence of different wavelengths towards the scattering zone. In the scattering zone, the different wavelengths scatter differently according to the wavelength and particle size. The scattered light is then captured, i.e. detected, using the sensors, which may be optimised for different wavelength. That is, their wavelength sensitivities differ from each other. The sensors produce sensor signals depending on their sensitivity characteristics and the amount of light hitting the sensors. Using the signals coming from the multiple wavelength optimised sensors 6, the content, i.e. concentration characteristics, of different particulate matter (PM) size fractions of the medium can be concluded. For example, it is possible to measure simultaneously PM0.5, PM2.5, PM10 (i.e. particles with sizes in the 0.5 µm, 2.5 µm and 10 µm class) and total suspended dust.

This particle size determination method can be carried out using instrumentation similar to that of FIG. 1 by increasing the number of light sources and sensors, which can be placed, as shown, all in essentially the same location, whereby the same light input and output openings can be used, or at different locations so that each source sensor pair has different input and output openings, or even a combination of these approaches. The different light sources can be formed in a single light source unit capable of modulating the wavelengths as desired. The sensors, for their part, can be located in single sensor unit comprising a plurality of sensors optimised for different wavelengths.

In general, a corresponding device for characterizing particle size distribution comprises a plurality of light sources having different wavelength characteristics, means for modulating in sequence the plurality of light sources in order to produce a plurality of said light rays at different wavelengths to the scattering zone, and a plurality of sensors adapted to detect scattered light at different wavelengths to provide sensor signals. Additionally, there are provided means for determining, based on the sensor signals, concentration characteristics of at least two different particle size fractions of the medium. As referred to above, for each wavelength, the device may operate using the same-sensor principle as discussed elsewhere in this document or in some other sensor measurement configuration and/or geometry.

The term "concentration characteristics" covers relative concentrations (e.g. the concentration of single size fraction to total particle concentration or concentration another size fraction) and absolute concentration.

Within the scope of the invention, it is also possible to envisage solutions differing from the solutions described above.

The following clauses represent embodiments:

1. Method for measuring the properties of particles contained in a medium on the basis of the scattering of a light ray travelling through the medium, characterized in that the light ray (2) can be guided through the scattering zone (4) more than once, so that both the scattered light (5) and the unscattered light can be measured using the same sensor (6).

2. Measuring device for measuring the properties of particles in a flue gas on the basis of the scattering of a right ray (2) travelling through the flue gas flowing in a measuring duct (4), characterized in that the light ray (2) can be led through the measuring duct more than once, so that both the scattered light (5) and the unscattered light can be measured using the same sensor (6).

3. Measuring device according to clause 2, wherein a measuring duct (4) arranged parallel to the actual flue continues through the measuring device with essentially the same dimensions as it comes to the measuring device from the actual flue.

4. Measuring device according to clause 2, wherein the dirtying of the optical elements of the measuring device by impurities in the flue gas is prevented by blowing a clean gas (3) past the light openings in the measuring duct (4).

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to "one embodiment" or "an embodiment" means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", i.e. a singular form, throughout this document does not exclude a plurality.

INDUSTRIAL APPLICABILITY

The present invention can be used for measuring the properties of particles in fluids, in a wide range of concentrations from particles in flue gases to clean rooms, or particles in liquids, such as sediment in water. One example of a practical application is measurement of dust in air, both in outdoor air and in indoor air.

LIST OF REFERENCE SIGNS 1 light source
2 light ray
3 clean-gas duct
4 measuring duct
5 light scattered from the particles
6 light sensor
7 mirror
8 mirros

CITATIONS LIST

Patent Literature

U.S. Pat. No. 4,024,407
EP 1969997
EP 0768521

The invention claimed is:

1. A method for measuring properties of particles contained in a medium on the basis of scattering of a light ray travelling through the medium in a scattering zone, comprising:
guiding the light ray through the scattering zone more than once, whereby a portion of light is scattered,
measuring both the scattered light and the unscattered light using the same sensor.

2. The method according to claim 1, wherein in the medium is a flue gas.

3. The method according to claim 1, wherein by guiding the light ray through the scattering zone, a portion of light is scattered from particles contained in the medium, the method further comprising the steps of:
guiding part of the scattered light scattered to a chosen angle, to the sensor, and
guiding the unscattered light ray having traveled through the medium along a straight line again, in particular using mirrors, through the scattering zone to the sensor.

4. The method according to claim 3, wherein the intensity of unscattered light is reduced for example in connection with mirrors or using filters or dimmers.

5. The method according to claim 1, comprising
guiding the light ray from a light source to the scattering zone and further to the sensor through light openings,
blowing clean gas past the light openings, in particular as laminar flow, in order to prevent contamination of optical elements used in the method.

6. The method according to claim 5, wherein the medium, in particular flue gas, is heated before feeding to the scattering zone.

7. The method according to claim 1, wherein the method further comprises:
separating a measurement flow from a flue gas flow, the measurement flow forming said medium containing said particles,
guiding said light ray to said measurement flow in a direction transverse to said measurement flow at said scattering zone whereby part of the light scatters to the sensor as scattered light,
guiding unscattered light passing the scattering zone using a first mirror past the scattering zone to a second mirror and using the second mirror again through the scattering zone to the sensor,
measuring both the unscattered and scattered light using the sensor.

8. The method according to claim 1, comprising
guiding a plurality of such light rays with different wavelengths through the scattering zone more than once, preferably in sequence, whereby light at each wavelength scatters differently depending on sizes of particle of the medium,
detecting the scattered light using a plurality of said sensors having different wavelength sensitivities,
determining concentration characteristics of at least two different particle size fractions of the medium.

9. A measuring device for measuring properties of particles in a medium, such as particles in a flue gas, on the basis of scattering of a light ray travelling through the medium flowing in a measuring duct comprising a scattering zone, the measuring device comprising: a light source for producing a light ray and a sensor, wherein the light ray is arranged to travel through the scattering zone more than once so that both scattered light and unscattered light are guided to the sensor, which is arranged to measure both the scattered light and the unscattered light.

10. The measuring device according to claim 9, wherein the light ray is arranged to travel from the light source for the first time through the scattering zone, whereby part of light is scattered to the sensor, and the unscattered light ray is further arranged to travel again through the scattering zone to the sensor.

11. The measuring device according to claim 10, comprising a first mirror and a second mirror, whereby the first mirror is arranged on the path of unscattered light traveled through the scattering zone for the first time and adapted to reflect light past the scattering zone to the second mirror, which is arranged to reflect the unscattered light again through the scattering zone to the sensor.

12. The measuring device according to claim 11, comprising means, such as means in connection with the mirrors, filters or dimmers, for reducing the intensity of unscattered light ray.

13. The measuring device according to claim 9, comprising light openings for guiding the light ray from the light source to the scattering zone and further to the sensor, and means for blowing clean gas past the light openings, in particular as laminar flow, for preventing contamination of optical elements of the measuring device.

14. The measuring device according to claim 9, comprising
- a plurality of light sources having different wavelength characteristics,
- means for modulating in sequence the plurality of light sources in order to produce a plurality of said light rays at different wavelengths to the scattering zone,
- a plurality of said sensors adapted to detect scattered light at different wavelengths to provide sensor signals,
- means for determining, based on the sensor signals, concentration characteristics of at least two different particle size fractions of the medium.

15. A measuring duct arranged in parallel with an actual flue, said measuring duct comprising: a measuring device according to claim 9, whereby the measuring duct continues through the measuring device with essentially the same dimensions as it comes to the measuring device from the actual flue.

* * * * *